United States Patent [19]

O'Hare

[11] Patent Number: 5,650,488
[45] Date of Patent: Jul. 22, 1997

[54] POLYPEPTIDE INHIBITOR OF THE REPLICATION OF HSV

[75] Inventor: Peter Francis Joseph O'Hare, Oxted, England

[73] Assignee: British Technology Group Limited, London, England

[21] Appl. No.: 196,260

[22] PCT Filed: Sep. 15, 1992

[86] PCT No.: PCT/GB92/01690

§ 371 Date: Feb. 16, 1994

§ 102(e) Date: Feb. 16, 1994

[87] PCT Pub. No.: WO93/06129

PCT Pub. Date: Apr. 1, 1993

[30] Foreign Application Priority Data

Sep. 18, 1991 [GB] United Kingdom ............... 9119940

[51] Int. Cl.⁶ .................... C07K 7/06; C07K 7/08
[52] U.S. Cl. .................... 530/327; 530/328; 530/329
[58] Field of Search .................... 530/328, 327, 530/326, 387.9, 388.1, 388.3, 389.1, 389.4, 329; 514/16, 15, 14

[56] References Cited

U.S. PATENT DOCUMENTS 5,245,010  9/1993  Greaves et al. .................... 530/327

FOREIGN PATENT DOCUMENTS

0410713A1  1/1991  European Pat. Off. .

OTHER PUBLICATIONS

A.Haigh C.S. "Interference with the assembly . . . " Nature, vol. 344, 15 Mar. 1990, London GB, pp. 257–259.

G. Werstuck C.S. "Mutational analysis of the herpes . . . " Gene, vol. 75, 1989 Amsterdam NL, pp. 213–224.

*Primary Examiner*—Frank C. Eisenschenk
*Attorney, Agent, or Firm*—Nixon & Vanderhye

[57] ABSTRACT

A polypeptide which inhibits the replication of Herpes Simplex Virus. The polypeptide contains the amino acid sequence 360–367 of the Herpes Simplex Virus protein Vmw 65 as shown in Sequence ID No. 1.

3 Claims, No Drawings

POLYPEPTIDE INHIBITOR OF THE REPLICATION OF HSV

This application is a 371 national stage application of PCT/GB92/01690, filed Sep. 15, 1992.

BACKGROUND OF THE INVENTION

1. Field of the Invention

This invention relates to a polypeptide which inhibits the replication of Herpes Simplex Virus (HSV) and like viruses and its therapeutic use against infections of such viruses.

2. Description of the Prior Art

HSV exists as several serotypes of which HSV-1 is one which is clinically significant in relation to cold sores. HSV-1 is a DNA virus which is transcribed and replicated within the cell nucleus. As with many other viruses, the genes are transcribed into mRNA at different times. Certain important genes which are the first to be transcribed are denoted immediate-early (IE) or "α". Their transcription is enabled by promoter sequences which lies to the 5' end or upstream of the ATG start codon of the gene. Further upstream from the promoter the IE genes have a distinctive nucleotide sequence which is a consensus (common) sequence TAATGARAT (where R=purine, i.e. can be G or A).

The IE genes of HSV are induced by a component of the virion, first identified by M. E. M. Campbell, J. W. Palfreyman and C. M. Preston, Journal of Molecular Biology 180, 1–19 (1984), as "Vmw 65". Vmw 65, which has also been referred to as VP16, is a tegument protein which lies between the vital membrane and the capsid. Vmw 65 is said to be "trans-acting" or "trans-activating". This language indicates merely that it is some soluble factor which acts on the viral DNA to regulate it. Yet another name for Vmw 65 is the α-Trans Inducing Factor or α-TIF, meaning that it acts on the viral DNA to induce transcription of the IE (α) genes.

M. E. M. Campbell et al., *loc. cit.* speculated that Vmw 65 might bind to the DNA in the TAATGARAT region, either directly or indirectly by modifying a host cell polypeptide. Later work, beginning with that of T. M. Kristie and B. Roizman, Proc. Natl. Acad. Sci. USA, 84, 71–75 (1987), has shown that the TAATGARAT region, which is termed a "cis-acting site" or the α-Trans Induction Cis-acting (α-TIC) site, does not bind directly to Vmw 65, but does bind to one or more host cell proteins. Various groups of workers have identified host cell proteins which bind both to the TAATGARAT region and to Vmw 65. They have been variously designated as "α-H1", "HC3", "octamer-binding protein", "OTF-1" "OCT-1" and "TAATGARAT Recognition Factor" (TRF), all of which are probably identical. The TRF nomenclature is used in this specification.

Current knowledge is summarised by O'Hare et al., (Nuc. Acid Res. 18 (3) 6871–6879 (1990)) who have isolated a fourth component of the induction complex which they have termed "complex forming factor" (CFF). This they believe to bind initially to Vmw 65 before the quaternary complex of Vmw 65, TRF, CFF and TAATGARAT sequence is formed. It is possible, and indeed it is expected, that further cellular factors are involved in complex formation to Induce gene transcription.

It would be desirable to block the formation of this complex and thereby block Induction of IE gene transcription of HSV. C. I. Ace et el al., J. Virology, 63, 2260–2269 (1989), have demonstrated that a virus mutant which lacks the ability to form such a complex with Vmw 65 and TRF replicates very poorly at low multiplicity of infection (MOI). Low MOI would be encountered clinically. Attempts have therefore been made to identify regions of Vmw 65 responsible for complex formation. It might then be possible to synthesise a short polypeptide which would compete with Vmw 65 In the formation of the complex.

S. J. Triezenberg, R. C. Kingsbury and S. L. McKnight, Genes & Development 2, 718–729 (1988) explored Vmw 65 structure/function with an assay for IE gene transcriptional induction and for the ability of Vmw 65 deletion mutants to inhibit IE transcriptional induction by normal Vmw 65. They showed that If the carboxy terminus of Vmw 65 was deleted, the protein would no longer induce IE transcription, but reported that this deleted protein could prevent IE induction by normal Vmw 65. Using various deleted forms of Vmw 65 they showed that the boundaries for this inhibitory activity (i.e. inhibition of normal Vmw 65 when the two are together) mapped at the N-terminus somewhere between amino acids 56 and 74 and at the C-terminus somewhere between 380 and 393. Since their proposition is that the competitive inhibitory activity its due to an interaction with a cellular intermediate, they claim that these boundaries may be the boundaries for interaction with this cellular intermediate. Note that the assay was for gene transcription, i.e. essentially for an "end product". Therefore, the inhibitory activity could actually take place at any of a wide range of steps, e.g. by saturating sites for transport of the virus into the nucleus of the cell.

G. Wertstuck and J. P. Capone, Gene 75, 213–224 (1989), have also explored Vmw 65 structure and function using measurements of the expression of a cat gene linked to an IE promoter region as an assay for the transcriptional induction function of Vmw 65. They found a total loss of IE induction activity when 4 or 5 amino acids were inserted into the Vmw 65 coding sequence at amino acids 178, 215, 335, 369 or 471 or when Vmw 65 was deleted in any of the following regions: amino acids 26-140, 26-177, 26-240, 142-177, 174-240, 179-412, 242-412, 331-412 and 331-470. In addition, in a similar assay to that used by Triezenberg et al, they examined the ability of the deleted mutants of Vmw 65 to competitively inhibit the IE induction function of normal Vmw 65. Competitive inhibition was obtained with mutants deleted from 331-470, 331-412, 242-412 or 186-490, indicating that the boundary of this competitive inhibiting activity mapped at an amino acid lower than 186. It Is noteworthy and illustrative of the complications resulting from using this sort of assay to attempt to relate structure of Vmw 65 to function, that the boundary mapped for competitive Inhibitory activity by Wetstuck and Capone differs substantially from that mapped by Triezenberg et. al., supra.

R. Greaves and P. O'Hare, Journal of Virology 63, 1641–1650 (April 1989), directly demonstrated that the acidic C-terminal domain of Vmw 65 (from amino acids 403 to the C-terminus) is not required for complex formation but that within the sequence of amino acids 317–403 there is a region which is required for complex formation.

C. I. Ace et al., J. Gert. Virology 69, 2595–2605 (1988) and Journal of Virology 63, 2260–2269 (May 1989) have performed biochemical studies of DNA-protein complex formation. This group has shown that insertion of a linker encoding a small number of amino acids (usually 4), at any of several of positions in the Vmw 65 sequence, directly prevents the ability of these altered proteins to form a complex with TRF. Amongst these, an insertion at amino acid 379 prevented the ability to form complex. In parellel, they confirmed that those mutants unable to form complex with TRF were unable to induce IE expression.

SUMMARY OF THE INVENTION

It has now been found that complex formation is inhibited by a polypeptide which consists of or includes the region of about amino acids 360–367 of Vmw 65. This sequence comprises the amino acids Arg Glu His Ala Tyr Ser Arg Ala as shown as SEQ ID No. 1 in the sequence listing section before the Claims. Thus the invention includes a polypeptide comprising at least a portion of the region 360–367 as shown in SEQ ID No. 1 of the Herpes Simplex Virus protein Vmw 65, or a conservatively modified variant thereof, which polypeptide is capable of use as an inhibitor of a virus which has a Vmw 65-type protein which forms a complex with one or more cellular factors for induction of gene transcription. It has been observed that the polypeptide shown in SEQ ID No 1 may be shortened and yet retain its activity as a virus inhibitor. Therefore the invention further includes a polypeptide having the amino acid sequence of at least the region 360–366 of the Herpes Simplex Virus protein Vmw 65, or a conservatively modified variant thereof, with the proviso that the polypeptide does not extend beyond amino acid 372 of the said protein.

The invention additionally includes a polypeptide having the amino acid sequence of at least the region 360–367 of the Herpes Simplex Virus protein Vmw 65, or a conservatively modified variant thereof, with the proviso that the polypeptide does not extend beyond amino acid 372 of the said protein.

The polypeptides of the present invention may be accompanied by a neighbouring flanking region of about 5 to 6 consecutive amino acids. These flanking regions may act to stabilise the inhibitory polypeptides of the invention and are referred to hereinafter as flanking stabilizing regions as distinct from the polypeptide regions that actually inhibit complex formation. The polypeptide comprising the region 355–367 of the Herpes Simplex Virus protein Vmw 65 is an example of a polypeptide of the present invention that includes a flanking stabilizing region. The region 360–367 being the polypeptide inhibitory region and the region 355–359 the flanking stabilizing region.

The invention includes the polypeptides per se, together with conservatively modified variants thereof, and their use as inhibitors of any virus which depends for its action on a Vmw 65-like protein, but, of course, particularly for Herpes Simplex Viruses and especially HSV type 1.

The invention further includes antibodies to the polypeptides of the invention and their use as inhibitors of vital replication and for other purposes.

The present invention is surprising in view of the teachings of earlier UK Patent Application Publication No. 2234246A (British Technology Group Limited, and its equivalent PCT Application Publication No. WO91/01329) disclosed a polypeptide of up to 40 consecutive amino acids of the Herpes Simplex Virus Vmw 65 protein consisting of or including the region 367–373 of the protein and its use as an inhibitor of viruses with a Vmw 65-like protein, e.g. HSV-1. That application- relied on a showing that inhibition of complex formation was associated with mutants of the C-terminal fragment of Vmw 65. The strict requirement of the presence of the region 367–373 in the inhibiting polypeptide was based on observation of the homology of this region with the terminal protein of the *B. subtilis* bacteriophage φ29—a protein involved in protein-protein and protein-DNA interactlone. In a subsequent paper R. Greaves and P. O'Hare (J. Virol. 64, 2716–2724 (1990)) showed that point mutations within the region 367–373 and downstream therefrom removed complex formation capabilities from Vmw 65. Thus both this earlier application and subsequent paper are directed towards the 367–373 region of Vmw 65 with the suggestion that further inhibition may be obtained by including more of the Vmw 65 sequence primarily towards the C-terminus, e.g. 360–390.

Description Of the preferred embodiments

The present invention has at its heart an experimental surprising showing that a region further towards the N-terminus than the region described in UK Patent Application Publication No. 2234246A is capable of inhibiting complex formation.

Polypeptides of the invention can be prepared by routine methods of synthesis, well known to those in the peptide field. For use as inhibitors of HSV replication in humans the polypeptides can be administered parenterally in a suitable inert diluent at a dose typically within the range 0.1 to 15 mg. per day. Topical administration, as an ointment or cream is also contemplated. Therefore, the invention further includes the use of the polypeptides as hereinbefore described in the manufacture of a medicament for the inhibition of viruses which have a Vmw 65-like protein especially HSV-1.

The invention also includes antibodies to the polypeptides of the invention, whether polyclonal, monoclonal or made by antibody engineering. Such antibodies are potentially of therapeutic value to block the Vmw 65 directly and also useful in the diagnosis of herpes virus infections. For example, they could be used to capture the Vmw 65 for a two site or sandwich assay, a labelled antibody directed to another epitope of Vmw 65 being used for detection of the captured Vmw 65. In order to produce the antibodies of the invention it is convenient to attach to the N-terminal end a cysteine residue, thereby providing an —SH termination. This enables the polypeptide to be coupled to (say) bovine serum albumin for the raising of antibodies, which can be immobilised in a conventional manner.

The invention is particularly applicable to the human Herpes Simplex Viruses Type 1 and 2 and to other herpes viruses which depend on Vmw 65 or a protein which is closely homologous in the relevant amino acid region for binding to a cellular factor to form a complex which induces IE gene expression.

The following Examples illustrate the invention.

EXAMPLE 1

The experiment for demonstration of peptide inhibition of quaternary complex assembly was as follows.

A nuclear extract of HeLa cells was prepared exactly as described by Dignam et al., Nucl. Acids. Res. 11 1475–1489, (1983) (This is a standard protocol for the preparation of extracts containing cellular DNA binding proteins). Polypeptides from Vmw 65 amino acids were synthesised by Cambridge Research Biochemicals Ltd., Cambridge, UK, under contract, in accordance with the sequence set forth above. 1 µl volumes of phosphate buffered saline containing increasing amounts (100 ng, 500 ng, 1 µg, 2.5 µg, 5µg) of the polypeptide (amino acids 360–367) was added to a standard amount of HeLa cell nuclear extract (1 µl extract per 2 µg polypeptide). After incubation at 20° C. for 30 minutes a 1 µl sample of Vmw 65 protein, purified as described by P. O'Hare et al., EMBO J. 7: 4231–4238 (1988) was added to the extract polypeptide mixtures and incubation continued for a further 5 minutes in a buffer containing 25 mM HEPES pH 7.9, 1 mM EDTA, 5 mM DTT, 100 mM KCl, 0.05% NP40 10% glycerol, and 2 µg of salmon sperm DNA. A $^{32}$P radioactively labelled probe present in excess and encompassing nucleotides −171 to −149 (numbered starting upstream of the site of mRNA transcription: the TAATGARAT sequence is at −162 to −154) of the immediate-early IE110K gene of HSV-1 was then added and incubation continued for a further 25 minutes. The products were then separated on 4% non-denaturing polyacrylamide gels at 200 volts for 2 hours. These procedures are essentially as described in O'Hare and Goding, Cell 52: 435–445 (1988). On autoradiography, the gels showed high molecular weight bands due to the radiolabelled TRF and TRF/Vmw 65/CFF complexes when there was zero concentration of any polypeptide. In the presence of the 360–367 polypeptide, the radiolabelled TRF/Vmw 65/CFF band became fainter with increasing concentration, becoming undetectable at concentrations between 500 ng and 1 μg. The radiolabelled band representing the TRF alone did not alter in intensity.

From the Table it can be seen that the polypeptides 360–367, 350–366 and 355–367 were effective in inhibiting complex formation.

TABLE

| Region of Vmw-65 (amino acid numbers) | Level of Inhibition |
| --- | --- |
| 360–367 | ++ |
| 360–366 | ++ |
| 355–367 | +++ |
| 360–365 | − |
| 360–364 | − |
| 360–363 | − |
| 361–367 | − |
| 362–367 | − |
| 363–367 | − |
| 361–366 | − |
| 361–365 | − |
| 361–364 | − |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: internal ( v i ) ORIGINAL SOURCE:
      ( A ) ORGANISM: Herpes simplex virus
      ( B ) STRAIN: HSV type 1

( x i ) SEQUENCE DESCRIPTION: SEQ ID NO:1:

Arg Glu His Ala Tyr Ser Arg Ala
   1                 5

EXAMPLE 2

The experiment described in Example 1 was repeated using a variety of polypeptides as shown in the Table below. The polypeptides tested included one comprising the region 360–366 of Vmw-65 and another comprising the region 355–367. This latter polypeptide is an example of a polypeptide of the present invention being flanked by a flanking stabilizing region. In the Table the results of the experiment are shown as follows: "+++" indicates a high level inhibition of complex formation, "++" indicates a lower level and so on. "−" indicates no inhibition of complex formation.

I claim:

1. A polypeptide having the amino acid sequence 360–367 of the Herpes Simplex Virus protein Vmw 65 as shown in SEQ ID No. 1.

2. A polypeptide having the amino acid sequence 360–366 of the Herpes Simplex Virus protein Vmw 65.

3. A polypeptide having the amino acid sequence 355 to 367 of the Herpes Simplex Virus protein Vmw 65.

* * * * *